United States Patent
Sumino

(10) Patent No.: US 6,916,651 B2
(45) Date of Patent: Jul. 12, 2005

(54) HEAT TREATED IMMOBILIZED MICROORGANISM SUPPORT FOR ENVIROMENT REMEDIATION

(75) Inventor: Tatsuo Sumino, Chiyoda-ku (JP)

(73) Assignee: Hitachi Plant Engineering & Construction Co., Ltd., Tokyo (JP)

(*) Notice: Subject to any disclaimer, the term of this patent is extended or adjusted under 35 U.S.C. 154(b) by 475 days.

(21) Appl. No.: 10/067,262

(22) Filed: Feb. 7, 2002

(65) Prior Publication Data

US 2002/0155584 A1 Oct. 24, 2002

(30) Foreign Application Priority Data

Feb. 21, 2001 (JP) .......................................... 2001-045209

(51) Int. Cl.⁷ ............................. C07F 3/00; B09B 3/00; C12N 11/02; C12N 11/10; C12N 11/04
(52) U.S. Cl. ................... 435/262.5; 210/601; 435/177; 435/178; 435/180; 435/182; 435/395
(58) Field of Search .................................. 435/174, 177, 435/178, 180, 182, 395, 262.5; 210/601

(56) References Cited

U.S. PATENT DOCUMENTS 4,791,061 A * 12/1988 Sumino et al. ............. 435/178

FOREIGN PATENT DOCUMENTS

| JP | 58-159894 | 9/1983 |
| JP | A 61-204089 | 9/1986 |
| JP | 62-166889 | 7/1987 |
| JP | 63-044994 | 2/1988 |
| JP | 05-092196 | 4/1993 |
| JP | 06-030773 | 2/1994 |
| JP | 08-116974 | 5/1996 |
| JP | 11-090473 | 4/1999 |
| JP | 2000-325979 | 11/2000 |

* cited by examiner

Primary Examiner—David M. Naff
(74) Attorney, Agent, or Firm—Oliff & Berridge, PLC

(57) ABSTRACT

The heated support can be manufactured by subjecting an immobilized microorganism support in which activated sludge is immobilized by entrapment to heat treatment. Thus, it is possible to support particular microorganisms at high concentrations in an immobilizing material without pure culturing of the microorganisms.

11 Claims, 8 Drawing Sheets

RELATIONSHIP BETWEEN HEATING TEMPERATURE AND NUMBER OF BACILLARY CELL (NUMBER OF CELLS WAS MEASURED AFTER SUPPORTS AND ACTIVATED SLUDGE WERE HEAT TREATED AND CULTURED)

SUPPORTS FOR TEST
(ENTRAPMENT-IMMOBILIZED ACTIVATED SLUDGE SUPPORTS)

US 6,916,651 B2

HEAT TREATED IMMOBILIZED MICROORGANISM SUPPORT FOR ENVIROMENT REMEDIATION

BACKGROUND OF THE INVENTION

1. Field of the Invention

The present invention relates to heated supports for efficiently carrying out biological treatment of inorganic and/or organic compounds in wastewater and in the air, and to methods for manufacturing the supports and for environment remediation with the supports.

2. Description of the Related Art

Biological treatment in which wastewater and sewage are treated with microorganisms is widely adopted due to a relatively low cost. However, some kinds of microorganisms grow at slow rates, are easily poisoned, or are difficult to grow in their environment, and as a result, biological treatment is not always an efficient process in some cases. Hence, treating processes have been already put into practice in which biological treatment is carried out using an immobilized microorganism support, in which activated sludge or specific microorganisms have been immobilized beforehand inside the support by entrapment so as to actively form an environment suitable for the growth of the microorganisms.

As immobilizing materials for supporting (holding) microorganisms inside the materials, gel materials are usually employed, and they are required to have no harm to the environment, undergo no microbial change nor degradation, possess high mechanical strength, have the capacity of supporting microorganisms in large amounts, and the like. Gel materials put into practice so far are polyethylene glycol based polymers, polyvinyl alcohol based resins, and others, as described in Japanese Patent Application Publication No. 61-204089. On the other hand, as microorganisms to be immobilized in a gel material by entrapment are utilized activated sludge and pure-cultured microorganisms.

Recently, bacilli that are bacteria belonging to *Bacillus subtilis* are attracting attention as the microorganism. These bacilli have superior properties in the so-called clean-up of environmental pollutants, such as degradation of oil materials and high-concentration BOD components, degradation and removal of foul order components, improvement in the flocculation of excess sludge produced in biotreatment, and degradation of COD components, and technology utilizing pure strains has been investigated.

In order to carry out biological treatment of environmental pollutants employing bacilli, an immobilized microorganism support in which bacillary cells dominate and are supported at high concentrations must be manufactured. Conventionally, it is necessary to immobilize pure-cultured bacilli in a gel material, as shown in FIG. 9.

In this case, however, pure-culturing requires culturing tanks and large amounts of medium, and additionally has a disadvantage of entailing production costs in excess due to requiring a long period for culturing and thus necessitating high labor costs.

SUMMARY OF THE INVENTION

The present invention has been developed in view of the above-described circumstances, and has as its object the provision of heated supports capable of supporting particular microorganisms at high concentrations in an immobilizing material without performing pure culture of the microorganisms and methods for manufacturing such supports and for environment remediation with the supports.

In order to achieve the above described object, the present invention is directed to a method for manufacturing a heated support, wherein an immobilized microorganism support is subjected to heat treatment, in which activated sludge is immobilized inside of the support by entrapment.

The present invention is also directed to a method for manufacturing a heated support, wherein at least one of monomers and prepolymers that are immobilizing materials for supporting microorganisms is polymerized in the presence of activated sludge while carrying out heat treatment.

According to the present invention, activated sludge is subjected to heat treatment not in naked conditions, but in conditions where the activated sludge has been entrapped in an immobilizing material, or during polymerization in a gelling reaction in which the activated sludge is entrapped in an immobilizing material, so that from the activated sludge in which plural kinds of microorganisms exist in mixture, particular microorganisms having heat resistance can be enriched in a dominance state within the immobilizing material, and at the same time the microorganisms that are in a dominance state can grow effectively in subsequent culture of the heated support.

Preferably, performing the heat treatment at temperatures in the range of not less than 40° C. and not more than 130° C. allows the provision of the heated support in which bacillary cells are enriched dominantly within the immobilizing material.

The present invention is also directed to a method for biological treatment by contacting a heated support having bacillary cells supported at a high concentration with at least one environmental pollutant of inorganic and/or organic pollutants forming oil materials, BOD components, COD components, and foul odor components. When compared to conventional immobilized microorganism supports without undergoing heat treatment (non-heated supports), it is possible to decompose and remove these environmental pollutants efficiently.

The present invention is also directed to a method for biological treatment by contacting a heated support having bacillary cells supported at a high concentration with excess sludge yielded by bio-treatment. When compared to conventional immobilized microorganism supports without undergoing heat treatment (non-heated supports), it is possible to improve the flocculation of excess sludge to advantage.

The present invention is also directed to a method for biological treatment by contacting a heated support having bacillary cells supported at a high concentration with water containing a water bloom or on which a water bloom may emerge. When compared to conventional immobilized microorganism supports without undergoing heat treatment (non-heated supports), it is possible not only to decompose and remove a water bloom effectively, but also to prevent a water bloom from emerging from the water on which a water bloom may emerge.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein.

DETAILED DESCRIPTION OF THE PREFERRED EMBODIMENTS

Hereunder preferred embodiments will be described in detail for heated supports and methods for manufacturing the same and for environment remediation therewith according to the present invention, in accordance with the accompanying drawings.

Figure 1:
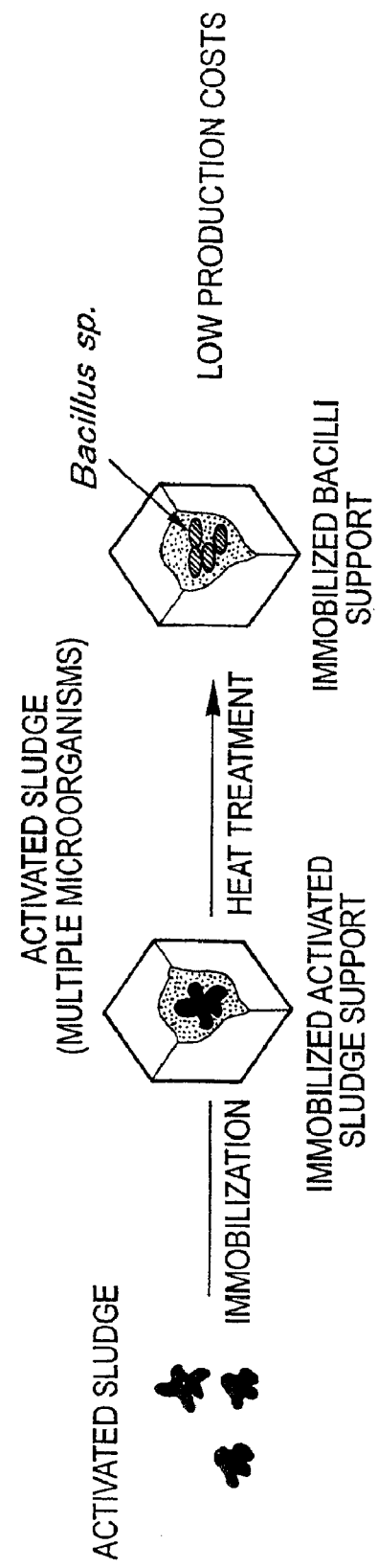
FIG. 1 is a conceptual illustration showing a method for manufacturing a heated support of the present invention.

FIG. 1 is a conceptual illustration showing a method for manufacturing a heated support of an embodiment of the present invention, in which as microorganism, Bacilli in activated sludge are enriched dominantly in an immobilizing material and supported at a high concentration.

As illustrated in FIG. 1, in a method for manufacturing a heated support of the present embodiment, activated sludge is immobilized in an immobilizing material by entrapment to manufacture an immobilized microorganism support which in turn is subjected to heat treatment. In another method for a heated support of the present embodiment, which is not shown, any one of monomers or prepolymers that are immobilizing materials is polymerized in the presence of activated sludge while carrying out heat treatment. Thus, a heated support of the present embodiment can be obtained. In these cases, the temperature of the heat treatment allowing bacillary cells to be enriched dominantly in an immobilizing material is preferably not less than 40° C. and not more than 120° C., and the period of the heat treatment is preferably not less than one minute and not more than 30 minutes.

That is, it is important to the present embodiment that activated sludge is subjected to heat treatment not in naked conditions, but in conditions where the activated sludge has been entrapped in an immobilizing material, or during polymerization in the gelling reaction in which the activated sludge is entrapped in an immobilizing material. Thereby, among plural kinds of microorganisms that exist in mixture in the activated sludge, bacilli that are bacteria resistant to heat remain selectively in the immobilizing material, and then result in a rapid growth. In consequence, the percentage in the number of the total cells at which bacillary cells are occupied in the immobilizing material can be increased significantly, so that heated supports can be manufactured that have bacillary cells supported in a dominance state. In addition, subsequent culture of the heated support also permits effectively growing the bacillary cells that are in a dominance state.

Figure 2:
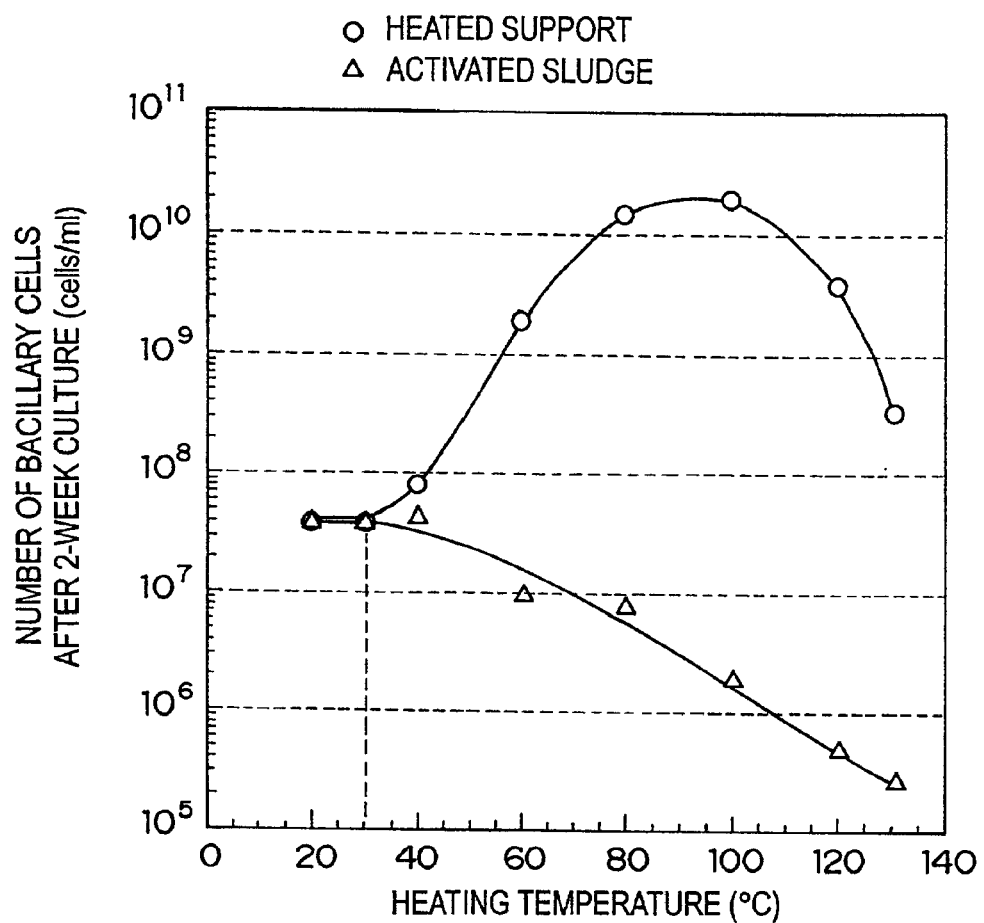
FIG. 2 is a graph showing the relationship between the temperature of the heat treatment and the number of bacillary cells.
Figure 3:
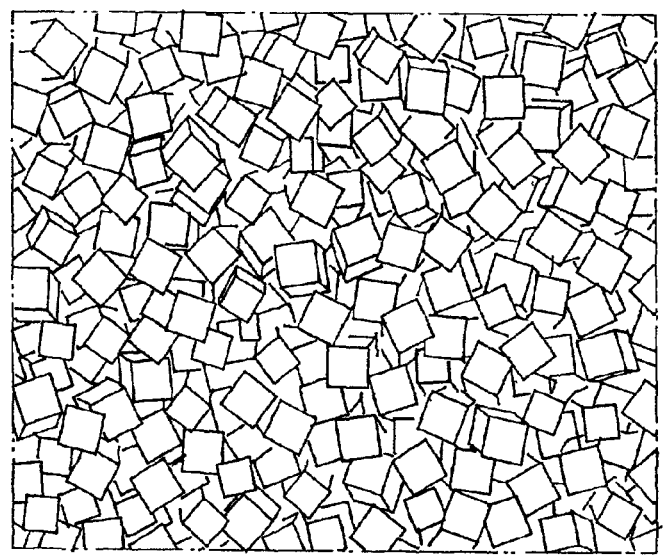
FIG. 3 is a view showing a number of immobilized microorganism supports before heat treatment which are cut into pellets of 3 mm per side.

FIG. 2 shows the results comparing the number of bacillary cells after culturing for two weeks between for heated supports of the present embodiment which were subjected to heat treatment at heating temperatures of 20° C. to 130° C. after activated sludge had been immobilized in an immobilizing material by entrapment and for activated sludge samples that had received heat treatment in naked conditions at heating temperatures of 20° C. to 130° C. In FIG. 2, the open circles represent heated supports, and the open triangles represent activated sludge samples.

As shown in FIG. 2, at heating temperatures not more than 30° C., the number of bacillary cells was at $10^7$ cells/ml level for both the heated support and activated sludge samples, and no difference was observed. However, the number of bacillary cells in the heated supports increased greatly when the temperatures exceeded 30° C. and reached a peak at 100° C. at which the number of bacillary cells was at $10^{10}$ cells/ml level. At higher temperatures, the number of bacillary cells decreased from $10^9$ cells/ml level at 120° C. to $10^8$ cells/ml level at 130° C. On the other hand, the number of bacillary cells in the activated sludge receiving the heat treatment in naked conditions began to decrease when the temperature exceeded 30° C., and the number of bacillary cells at 120° C. reduced down to $10^5$ cells/ml level. In FIG. 2, the number of bacillary cells in the activated sludge itself receiving the heat treatment in naked conditions was determined, but similar results were also obtained with respect to the number of bacillary cells after the activated sludge receiving the heat treatment in naked conditions was immobilized by entrapment in the same immobilizing material as that used for the heated supports of the present embodiment. The reason why the bacillary cells were not grown readily at 20° C. to 30° C. in FIG. 2, is likely that the heat treatment is insufficient, and thus the growth of other contaminated cells takes place, inhibiting the growth of the bacillary cells due to the interaction with the contaminated cells.

Figure 9:
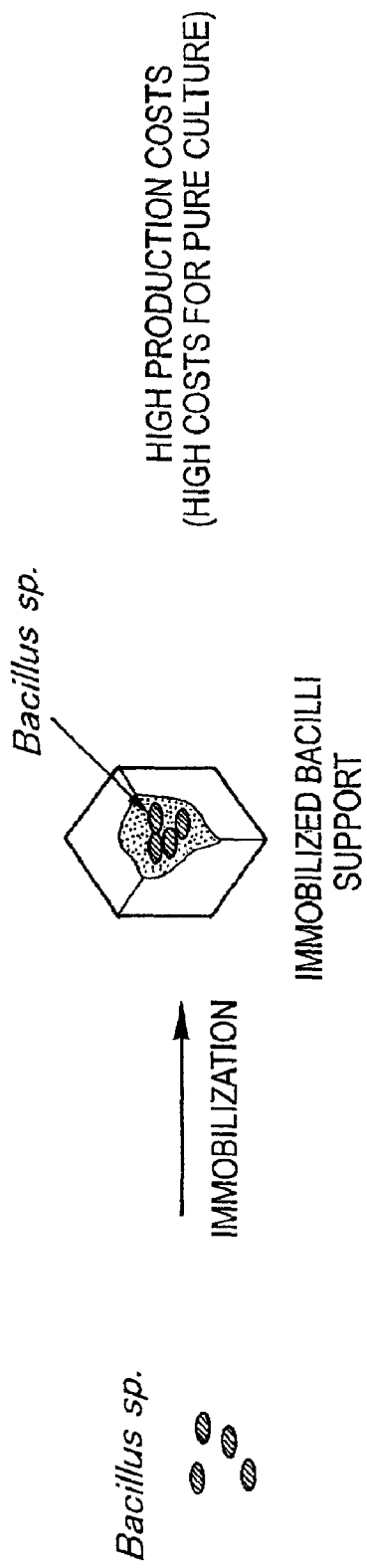
FIG. 9 is a conceptual illustration of a conventional immobilization method for immobilizing bacilli after pure culturing.

As can be understood from these results, even if since bacilli are bacteria resistant to heat, activated sludge is subjected to heat treatment in naked conditions before an immobilized microorganism support is manufactured by a conventional manufacturing method as shown in FIG. 9, it is impossible to grow the bacillary cells within the immobilized microorganism support manufactured. That is, as described above, in the manufacture of the heated support of the present embodiment, it is important that activated sludge is subjected to heat treatment not in naked conditions, but in conditions where the activated sludge has been entrapped in an immobilizing material or in the process of polymerization that is a process for entrapping the activated sludge. The heating temperature to obtain heated supports in which bacillary cells are enriched at high concentrations is preferably such that the number of the bacillary cells can be ensured at $10^8$ cells/ml level or higher, not less than 40° C. and not more than 130° C., and more preferably, not less than 60° C. and not more than 120° C., which is capable of ensuring the number of the bacillary cells at $10^9$ cells/ml level or higher.

As immobilizing materials employed in the manufacture of the heated supports of the present embodiment can be used monomethacrylates, monoacrylates, dimethacrylates, diacrylates, trimethacrylates, triacrylates, tetraacrylates, urethane acrylates, epoxy acrylates and others, polyvinyl alcohols, acrylamide, photo-curing polyvinyl alcohols, photo-curing polyethylene glycols, photo-curing polyethylene glycol polypropylene glycol prepolymers, and others.

Furthermore, the heated support of the present embodiment in which bacillary cells have been supported at high concentrations as described above allows effective degradation and removal of environmental pollutants described below by contacting the heated support with environmental pollutants, thereby carrying out biological treatment.

Environmental pollutants that can be biologically treated effectively by the bacilli include mainly oil materials (hexane extract), BOD components, COD components in wastewater, and foul odor components in the air such as mercaptan, hydrogen sulfide, ammonia, as the target.

Also, the heated support of the present embodiment in which bacillary cells have been supported at high concentrations can improve the flocculation of excess sludge yielded by biological treatments employing activated sludge.

In addition, the heated support of the present embodiment in which bacillary cells have been supported at high concentrations can not only degrade and remove effectively a water bloom in the water, but also prevent in advance the emergence of a water bloom with respect to the water on which a water bloom may emerge.

In embodiments of implementing the present embodiment, explanation is given by means of examples in which bacillary cells are enriched at high concentrations in an immobilizing material, but the present embodiment is not intended to be limited to bacilli. The present embodiment will make it possible to enrich, in a dominance state, specific microorganisms having heat resistance in an immobilizing material from activated sludge in which multiple kinds of microorganisms exist in mixture, and at the same time to grow effectively the microorganisms that are in a dominance state in subsequent culturing of the heated support.

EXAMPLES

The following describes Examples in which comparison tests on the bacilli dominance state and the treatment performance were carried out for a heated support of the present embodiment and a conventional immobilized microorganism support without heat treatment (hereinafter referred to as "non-heated support").

An immobilized microorganism support prior to heating was formed into pellets of 3 mm per side, as shown in FIG. 3, after immobilizing activated sludge collected from a sewage treatment plant A in Chiba Prefecture, Japan by entrapment with polyethylene glycol based prepolymer, and this immobilized microorganism support prior to heating was used as sample of a non-heated support. Two hundred milliliters of the immobilized microorganism support and three hundred milliliters of tap water were placed into a one-liter Erlenmeyer flask and subjected to heat treatment at 100° C. for 12 minutes in an autoclave, and the immobilized microorganism support after heating was used as sample of a heated support.

Table 1 represents the composition of the immobilized microorganism support prior to heating.

TABLE 1

| Immobilized microorganism support | |
|---|---|
| Activated sludge | 2% |
| Immobilizing material | 10% |
| Water content | 88% |

FIG. 4 is a schematic view of an experimental apparatus 10 for continuous treatment operation in which comparison tests on the bacilli dominance state and the treatment performance were carried out.

The experimental apparatus 10 had two attached aeration tanks 12, 12 with a volume of two liters, shown in FIG. 4, in which 200 ml of heated support A was added to one aeration tank 12 which was used as an experimental apparatus for the heated support, and 200 ml of non-heated support B was added to the other aeration tank 12 which was used as an experimental apparatus for the non-heated support. In these cases, the filling factor of the support in each aeration tank 12 was set to be same, 10%, for both the experimental apparatus 10. Synthetic wastewater was allowed to continuously enter the aeration tank 12 at the top, and the treated water after treating was allowed to exit through a net (screen) against the outflow of the support 14, which was provided on the side of the inside of the aeration tank. The synthetic wastewater was supplied at a flow rate of 11 ml/min., and continuous treatment operation was carried out such that the retention time in the aeration tank 12 was 3 hours. The net against the outflow of the support 14 utilized one with 2 mm opening, made of polyvinyl chloride. An air supplying tube 16 was provided for supplying oxygen into the aeration tank 12 and stirring the heated support, and allowed aeration into the synthetic wastewater in the aeration tank 12 at an aeration flow of 5 L/min. The temperature of the synthetic wastewater was set at 20° C.

Example 1

First, there is given an explanation of results of the examination of the bacilli dominance state using the experimental apparatus 10 shown in FIG. 4.

Table 2 represents the composition of the synthetic wastewater used in the examination of the bacilli dominance state.

TABLE 2

| Synthetic wastewater | |
|---|---|
| Components | Concentration (g/L) |
| Peptone | 21 |
| Meat extract | 16 |
| Urea | 4 |
| NaCl | 1.2 |
| KCl | 0.56 |
| $MgSO_4 \cdot 7H_2O$ | 0.4 |
| $Na_2HPO_4 \cdot 12H_2O$ | 4.0 |
| $CaCl_2 \cdot 2H_2O$ | 0.56 |

Table 3 represents the composition of standard agar medium used for determining the number of bacterial cells within the heated support A and the non-heated support B.

TABLE 3

| Standard agar medium | |
|---|---|
| Components | Concentration (g/L) |
| Yeast extract | 2.5 |
| Peptone | 5.0 |
| D(+)-glucose | 1.0 |
| Agar | 15 (in winter), 18 (in summer) |

FIG. 5 shows the state of colonies grown after homogenizing each of the heated support A and the non-heated support B prior to continuous operation and plate culturing with dilution on standard agar medium of Table 3. As indicated in FIG. 5, the heated support A resulted in the growth of single white colonies, whereas the non-heated support B resulted in the growth of various colonies whose color were white, yellow, and others. The white colonies grown from the heated support A were identified preliminarily with an identification kit of bioMerieux with the result that they could be concluded to be of bacilli. This indicates that heat treatment allows bacillary cells to be enriched in the support A in a dominance state.

Figure 4:
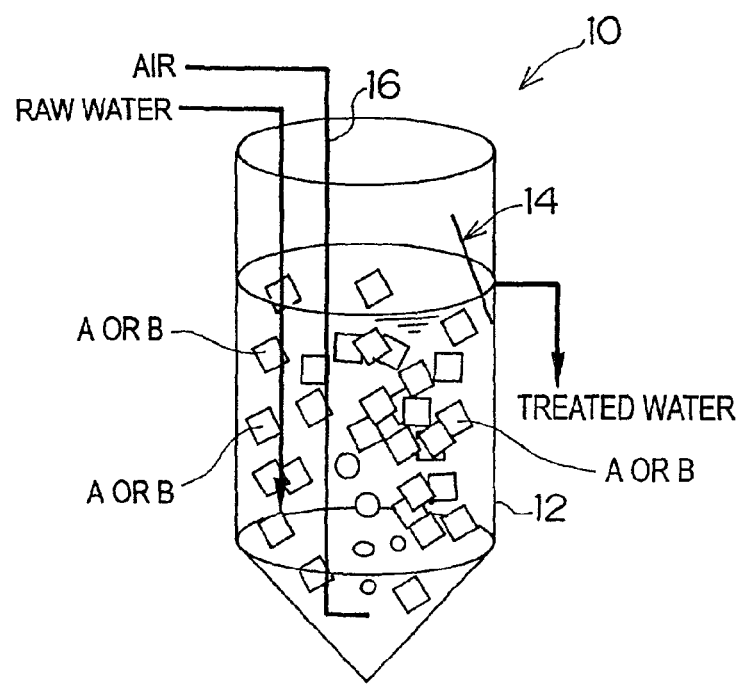
FIG. 4 is a schematic view of an experimental apparatus in which continuous treatment operation was done for the heated and non-heated supports.
Figure 5:
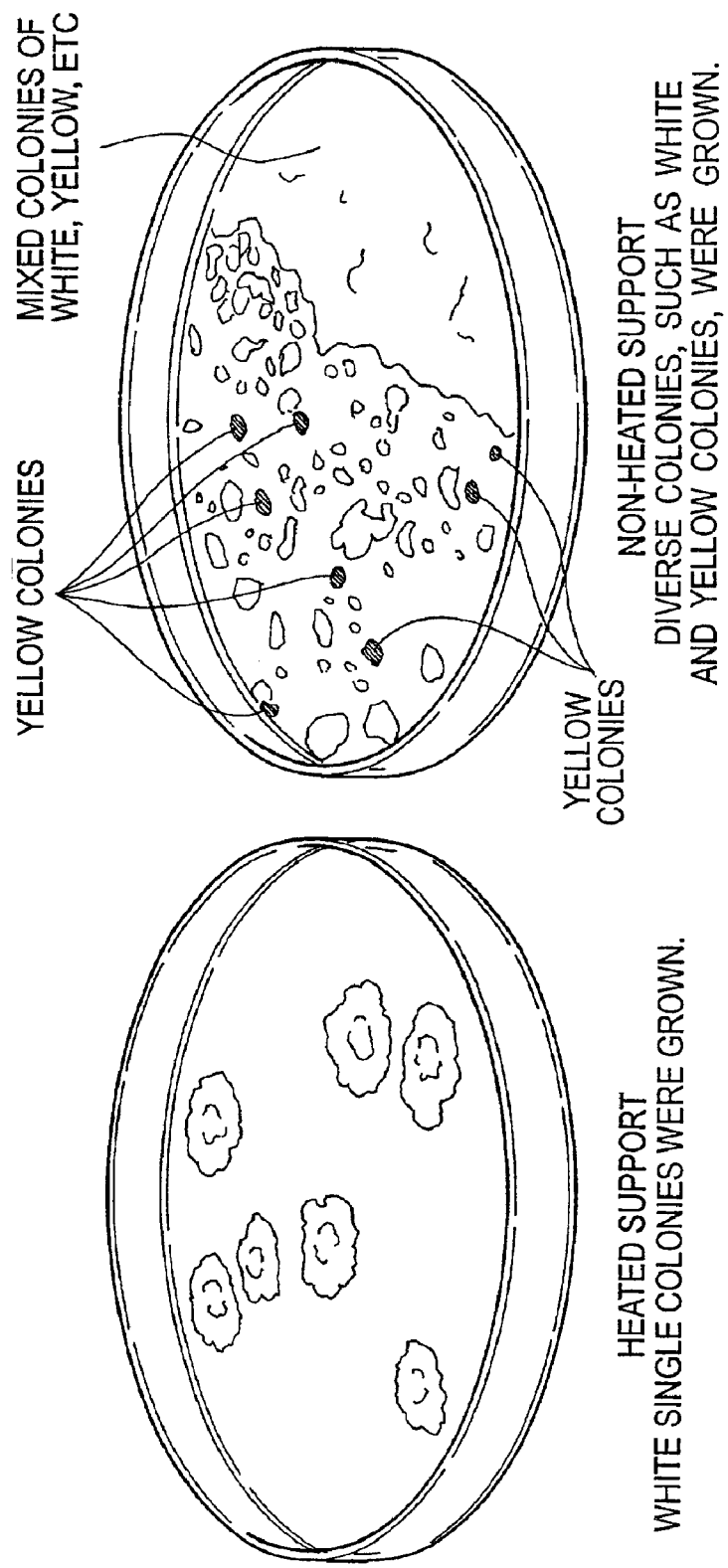
FIG. 5 is views of grown colonies resulting from culturing the heated and non-heated supports prior to the continuous treatment operation on standard agar medium.

Next, the heated support A and the non-heated support B were subjected to a continuous treatment operation of 6 months in the experimental apparatus 10 shown in FIG. 4, using the synthetic wastewater of Table 2 composed mainly of peptone and meat extract. By which, assessment was conducted as to what changes in the bacilli dominance state before the continuous operation would be brought about, that is, the stability of the bacilli dominance state.

Figure 6:
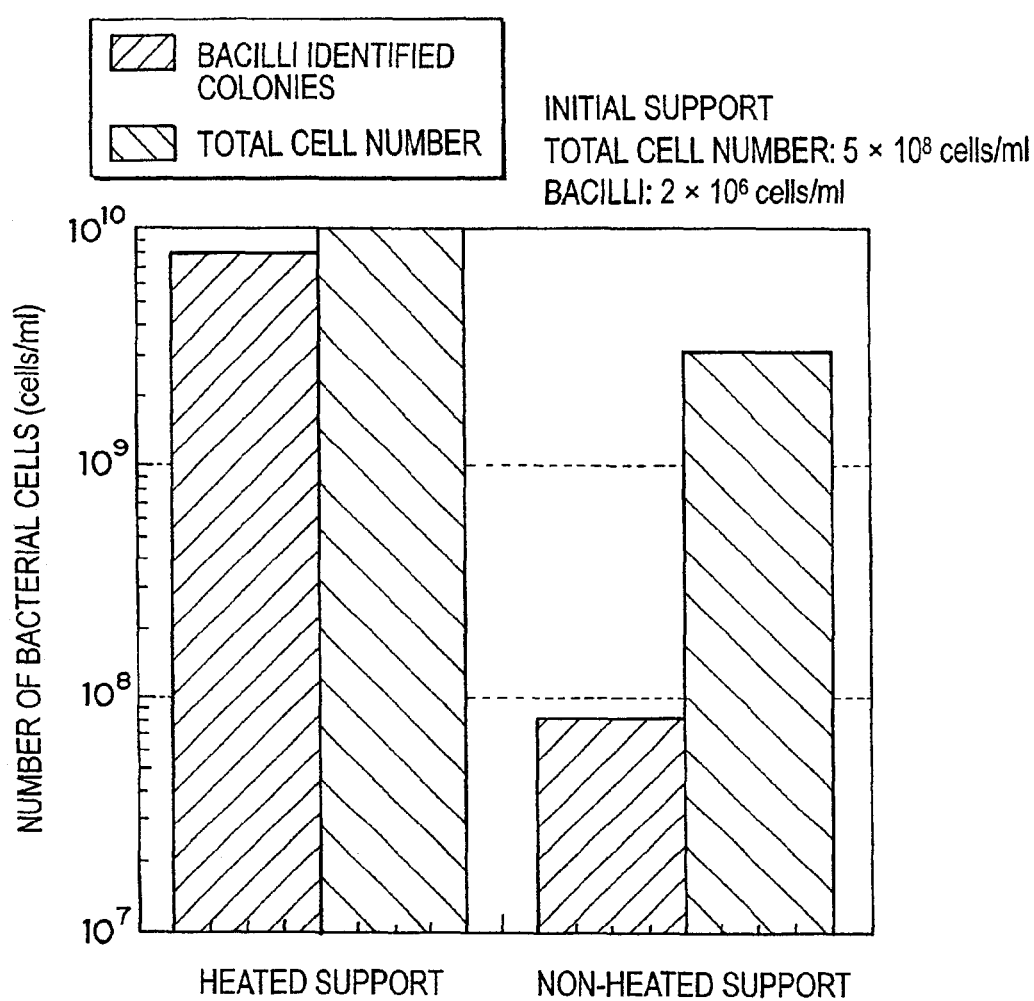
FIG. 6 is a graph obtained by counting the number of the total cells and bacillary cells in the heated and non-heated supports after completing the continuous treatment operation.

FIG. 6 is a graph which with respect to the heated support A and the non-heated support B after completing the continuous treatment operation, resulted from the determination of the number of the total cells and the bacillary cells in the supports A and B. The number of the total cells before the continuous operation (i.e., in the initial support) was $5 \times 10^8$ cells/ml, and the number of bacillary cells was $2 \times 10^6$ cells/ml.

As can be understood from FIG. 6, for the heated support A after completing the continuous treatment operation, the number of the total cells was $1 \times 10^{10}$ cells/ml, and the number of bacillary cells was $8.5 \times 10^9$ cells/ml. That is, in the case of the heated support A, almost all of the total cells increased by the continuous treatment operation resulted from the growth of the bacillary cells. On the other hand, for the non-heated support B, although the number of the total cells was increased to $2 \times 10^9$ cells/ml, the number of bacillary cells was $6 \times 10^7$ cells/ml, and the occupied ratio of the bacillary cells to the total cells was significantly low, when compared to the heated support A.

Figure 7:
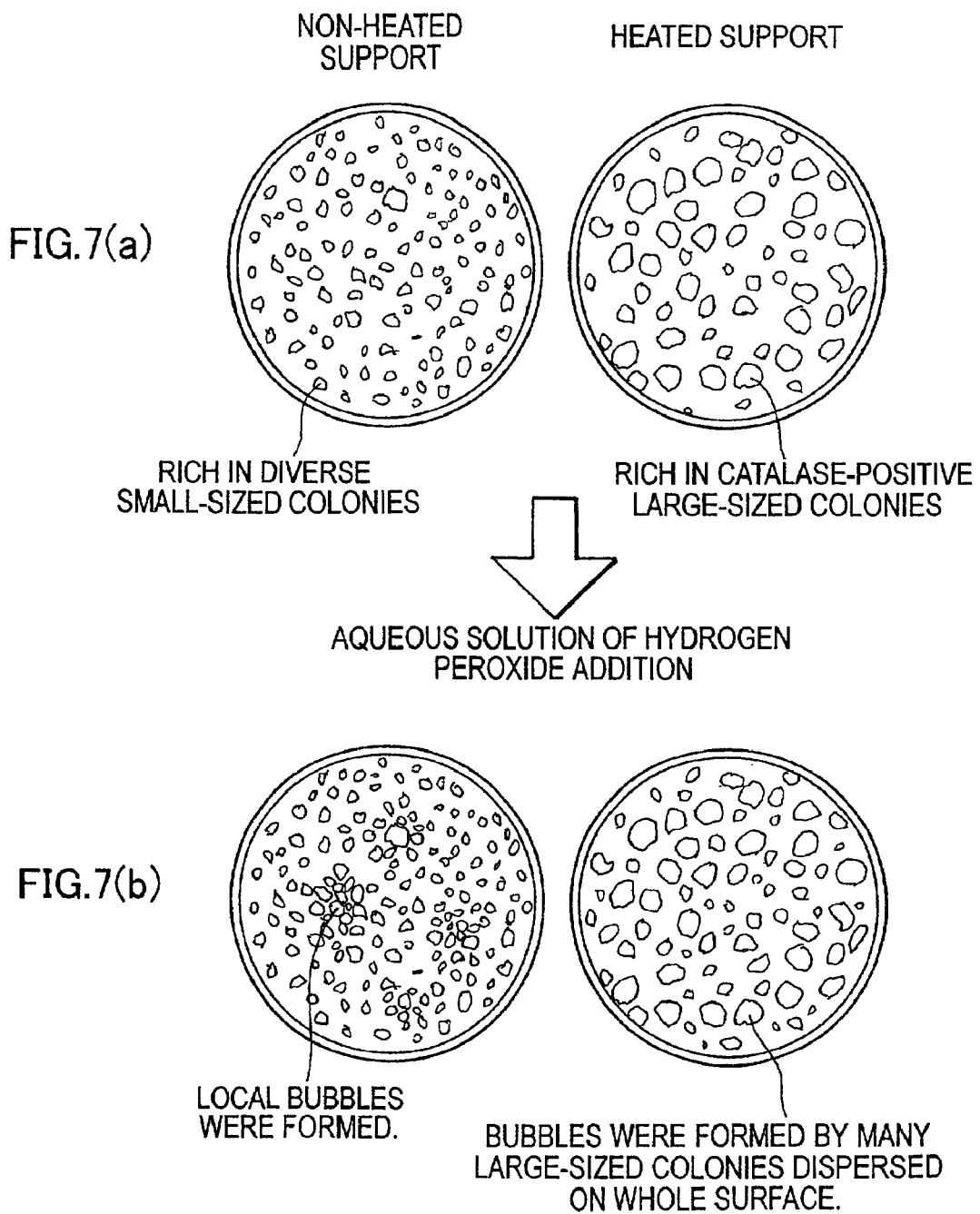
FIGS. 7(a) and 7(b) are views of grown colonies resulting from culturing the heated and non-heated supports after completing the continuous treatment operation on standard agar medium.

FIGS. 7(a) and 7(b) are views showing the morphology of colonies on plate culturing with dilution, with respect to the heated support A and the non-heated support B after the completing continuous treatment operation.

As shown in FIG. 7(a), the non-heated support B resulted in the growth of diverse small-sized colonies of white and yellow in color, whereas the heated support A resulted in the growth of almost uniform, large-sized colonies. FIG. 7(b) represents views at the time of applying a 3% aqueous solution of hydrogen peroxide to the colonies. The non-heated support B gave local bubbles, whereas the heated support A gave vigorous bubbles on the whole surface, and there was observed strong catalase activity that is a piece of evidence that the large-sized colonies are of bacilli. Furthermore, the large-sized colonies from the heated support A were subjected to identification using an identification kit of bioMerieux, and according to its results, could be concluded to be of bacilli.

From the results of FIGS. 5, 6, 7(a) and 7(b), it can be understood that in the heated support A, bacillary cells are always present dominantly, whether before or after the continuous treatment operation, and it has a good stability of the bacilli dominance state. This implies that the heated support A allows the enrichment culture of bacillary cells by a continuous treatment operation.

Example 2

This example describes results of the examination of the treatment performance by bacillary cells using the experimental apparatus 10 shown in FIG. 4.

Tests on the treatment performance utilized the same heated support A and non-heated support B as those used in the continuous treatment operation described above, and batch treatments were carried out to demonstrate the possibility of achieving treatment at high concentrations, wherein the synthetic wastewater in each aeration tank 12 of the experimental apparatuses 10 for the heated support A and the non-heated support B was replaced with a synthetic wastewater having 170 mg/L TOC (Total Organic Carbon). In the batch treatment, changes in decreasing the TOC concentration were measured over time. TOC measurements of the resulting treated water were made on filtrated solution resulting from filtering the treated water through 5A filter paper, and the rate of removing TOC was studied for the heated support A and non-heated support B.

The rate of removing TOC can be calculated according to the following equation (1):

$$ds/dt = K \times s \tag{1}$$

wherein, s: a TOC concentration in the wastewater (mg/l), t: time (h), and

K: a removal rate constant (l/h).

Figure 8:
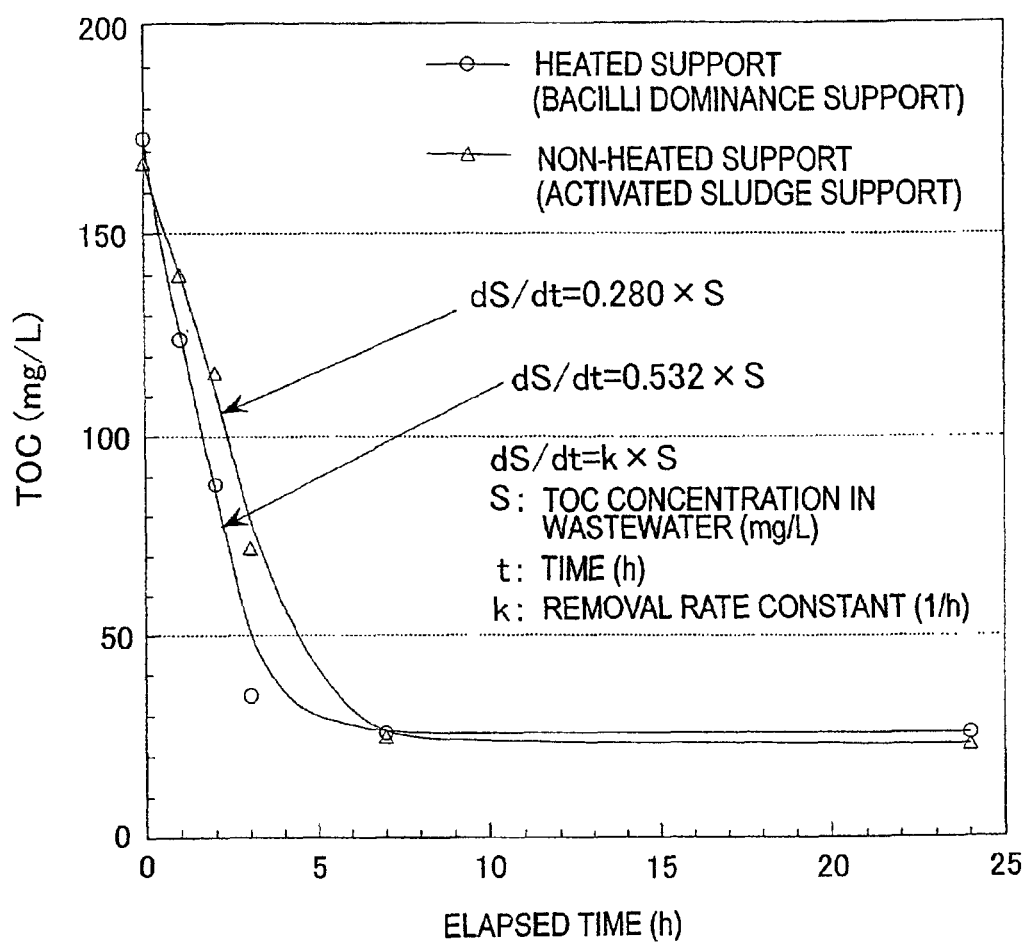
FIG. 8 is a graph showing the removal performance of TOC by the heated and non-heated supports.

The results are shown in FIG. 8.

As can be understood from FIG. 8, the heated support (bacilli dominance support) A had a rate of removing TOC of 0.532 $h^{-1}$, the non-heated support (activated sludge support) B had a rate of removing TOC of 0.280 $h^{-1}$, and thus the rate of removing TOC of the heated support A was about twice as high as that of the non-heated support B. This means that in the case of the wastewater in which the TOC concentration is intermediate concentrations (loads) in the order of 170 mg/l, the heated support A has treatment performance about twice as high as that of the non-heated support B.

Example 3

In Example 3, with respect to each of the heated support A and the non-heated support B, tests were carried out on the removal performance of BOD components, COD components, SS (suspended substances), the oil materials (n-hexane extract) at a food processing plant.

After completing the tests in Example 1, the synthetic wastewater in the aeration tank 12 was replaced with an effluent from the food processing plant, which in turn was subjected to a continuous treatment with a retention time of four hours.

The results are shown in Table 4.

TABLE 4

|  | Raw water (mg/L) | Treated water by the present embodiment (mg/L) | Treated water by a conventional method (mg/L) |
| --- | --- | --- | --- |
| BOD | 560–600 | 20 or less | 20–58 |
| COD | 330–480 | 20–40 | 58–120 |
| SS | 60–90 | 20 or less | 20 or less |
| n-hexane extract | 140–230 | 1 or less | 2–12 |

As can be understood from Table 4, the treated water according to the present embodiment employing the heated support A displayed good results in terms of BOD, COD, and an n-hexane extract, compared with the treated water according to a conventional method employing the non-heated support B. In particular, good performance was obtained with respect to the degradation of the COD components and the oil materials that were an n-hexane extract. Reasons for good performance of degrading the COD components are likely that bacilli catalase radically oxidizes the COD components.

Example 4

Example 4 describes the treatment performance of degrading a water bloom with respect to the heated support A and the non-heated support B.

For a heated support A used in Example 4, 200 ml of immobilized microorganism support prior to heat treatment and 300 ml of tap water were placed into a one-liter Erlenmeyer flask, and heat treated in an autoclave at 60° C. for 15 minutes. As in Example 1, 200 ml of the heated support thus manufactured was placed into a two-liter aeration tank 12 for the heated support and cultured first for one week in the synthetic wastewater indicated in Table 2. After one week culturing, the synthetic wastewater in the aeration tank 12 was changed to lake water containing a water bloom (containing $10^5$ cells/ml water bloom) and a continuous treatment was carried out at a retention time of 24 hours.

As a conventional procedure, a non-heated support B was placed into the aeration tank 12 for the non-heated support, and culturing was carried out in the synthetic wastewater indicated in Table 2 as in Example 4, followed by changing it to lake water containing a water bloom (containing $10^5$ cells/ml water bloom) and carrying out a continuous treatment at a retention time of 24 hours.

The results shows that the water bloom in treated water with the heated support A was reduced consistently down to $10^2$ cells or less, whereas the water bloom in treated water with the non-heated support B was at $10^4$ to $10^5$ cells/ml and the content of water bloom in the raw water was not changed significantly.

Example 5

Example 5 describes the removal of foul odor components such as mercaptan, hydrogen sulfide, ammonia, and others in the air.

In tests, a fixed filtration layer was provided in an about two-liter column, 5 cm in diameter and 100 cm in height, so that the filling factor was 70%, and air containing mercaptane was flowed into the column at the bottom and flowed out through the fixed filtration layer at the top. The concentration of the mercaptane in the influent and exhausted gasses was measured to determine the removal ratio. The retention time of the gas in the column was two minutes.

Similarly, air containing hydrogen sulfide and air containing ammonia were treated.

The results show that a removal ratio of 99% was achieved for each case of mercaptane, hydrogen sulfide, and ammonia.

As described above, according to heat supports in accordance with the present invention, methods for manufacturing them, and their supports, it is possible to support a particular kind of microorganisms at high concentrations in an immobilizing material without pure culturing of the microorganism.

Therefore, using the heated supports of the present invention, environmental pollutants could be degraded and removed effectively, compared to conventional non-treated supports without heat treatment.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. A method for manufacturing a heated support, comprising subjecting an immobilized microorganism support, in which activated sludge is immobilized inside of the support by entrapment, to heat treatment, wherein the heat treatment is conducted at a temperature of not less than 40° C. and not more than 130° C.

2. A heated support manufactured by the method for manufacturing a heated support according to claim 1.

3. A method for environment remediation, comprising contacting the heated support according to claim 2 with at least one of environmental pollutant chosen from the group consisting of BOD components, COD components, and foul odor components, thereby carrying out biological treatment.

4. A method for environment remediation, comprising contacting the heated support according to claim 2 with excess sludge yielded by bio-treatment, thereby carrying out biological treatment.

5. A method for environment remediation, comprising contacting the heated support according to claim 2 with one of water containing a water bloom and water on which a water bloom may emerge, thereby carrying out biological treatment.

6. A method for manufacturing a heated support, comprising polymerizing at least one of monomers and prepolymers that are immobilizing materials for supporting microorganisms in the presence of activated sludge while carrying out heat treatment, wherein the heat treatment is conducted at a temperature of not less than 60° C. and not more than 130° C.

7. A heated support manufactured by the method for manufacturing a heated support according to claim 6.

8. A method for environment remediation, comprising contacting the heated support according to claim 7 with at least one of environmental pollutant chosen from the group consisting of BOD components, COD components, and foul odor components, thereby carrying out biological treatment.

9. A method for environment remediation, wherein the heated support according to claim 7 is made contact with excess sludge yielded by bio-treatment, thereby carrying out biological treatment.

10. A method for environment remediation, comprising contacting the heated support according to claim 7 with one of water containing a water bloom and water on which a water bloom may emerge, thereby carrying out biological treatment.

11. The method according to claim 1, wherein the heat treatment is performed for a period of not less than 1 minute and not more than 30 minutes.

* * * * *

UNITED STATES PATENT AND TRADEMARK OFFICE
CERTIFICATE OF CORRECTION

PATENT NO. : 6,916,651 B2
DATED : July 12, 2005
INVENTOR(S) : Tatsuo Sumino

It is certified that error appears in the above-identified patent and that said Letters Patent is hereby corrected as shown below:

Title page,
Item [54], Title, should read:
-- HEAT TREATED IMMOBILIZED MICROORGANISM SUPPORT FOR ENVIRONMENT REMEDIATION --.

Signed and Sealed this

Twenty-seventh Day of September, 2005

JON W. DUDAS
*Director of the United States Patent and Trademark Office*